United States Patent [19]

Inada

[11] Patent Number: 4,645,741
[45] Date of Patent: Feb. 24, 1987

[54] MODIFIED LIPASE

[75] Inventor: Yuji Inada, Tokyo, Japan

[73] Assignee: Bellex Corporation, Tokyo, Japan

[21] Appl. No.: 687,635

[22] Filed: Dec. 31, 1984

[30] Foreign Application Priority Data

Jan. 17, 1984 [JP] Japan .................................. 59-6129

[51] Int. Cl.$^4$ .......................... C12P 7/64; C12P 7/62; C12N 9/96; C12N 9/20
[52] U.S. Cl. .................................. 435/134; 435/135; 435/188; 435/198
[58] Field of Search ............... 435/198, 197, 188, 134, 435/135

[56] References Cited

U.S. PATENT DOCUMENTS 4,179,337  12/1979  Davis et al. ........................ 435/181

OTHER PUBLICATIONS

Abuchowski et al, "Alteration of Immunological Properties of Bovine Serum Albumin by Covalent Attachment of Polyethylene Glycol" J. Bio. Chem., vol. 252, No. 11, pp. 3578-3581 (1977).

Abuchowski et al, "Effect of Covalent Attachment of Polyethylene Glycol on Immunogenicity and Circulating Life of Bovine Liver Catalase" J. Bio. Chem. vol. 252, No. 11, pp. 3582-3586, (1977).

T. Yoshimoto et al, "Modified Lipase having High Stability and Various Enzymic Activities in Benzene, and its Re-use by Recovering from Benzene Solution", Biotechnology Letters, vol. 6, No. 6, pp. 337-340 (1984).

Yuji Inada et al, "Ester Synthesis Catalyzed by Polyethylene Glycol-Modified Lipase in Benzene", Biochemical and Biophysical Research Communications, vol. 122, No. 2, (1984), pp. 845-850.

K. Takahashi et al, "Modified Lipoprotein Lipase Catalyzes Ester Synthesis in Benzene", Enzyme 32, pp. 235-240, (1984).

Primary Examiner—Lionel M. Shapiro
Attorney, Agent, or Firm—Frishauf, Holtz, Goodman & Woodward

[57] ABSTRACT

A modified lipase, comprising lipase molecules which are partially substituted with an active derivative of a polyalkylene glcyol having a hydrophobic group at the terminal end.

13 Claims, 2 Drawing Figures

MODIFIED LIPASE

BACKGROUND OF THE INVENTION

This invention relates to a modified lipase, which is soluble in organic solvents and can also maintain the enzymic activity even in organic solvents.

Generally speaking, utilization of an enzyme is limited to the reaction in an aqueous system, because an enzyme will lose its activity when it comes into contact with organic solvents or it is insoluble in organic solvents. Accordingly, if a modified enzyme soluble in organic solvents and capable of exhibiting enzymic activity can be obtained by chemical modification of an enzyme, there is the possibility that the enzymatic reaction may be carried out in organic solvents in the manufacturing steps or a water-insoluble substance may be used as the substrate, whereby the scope of industrial utilization of enzymes will be markedly enlarged.

Lipase is an enzyme which catalyzes irreversible hydrolysis and synthesis of fat. Since most of substrates are insoluble in water, if it is possible to carry out the enzymatic reaction in organic solvents, the scope of utilization of lipase will be enlarged such as decomposition and synthesis of various kinds of esters, modification of fats through interesterification, etc.

SUMMARY OF THE INVENTION

The present inventors have attempted to chemically modify lipase, in order to solve these problems, and obtained a modified lipase which is soluble in organic solvents and has retained its enzymic activity to accomplish the present invention.

The present invention provides a modified lipase, comprising lipase molecules partially substituted with an active derivative of a polyalkylene glycol having a hydrophobic group at a terminal end.

DESCRIPTION OF PREFERRED EMBODIMENTS OF THE INVENTION

Figure 1:
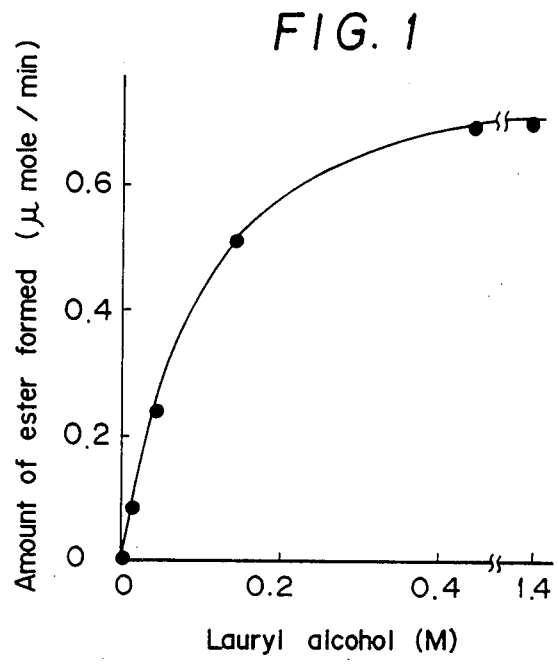
FIG. 1 and FIG. 2 show syntheses of esters with the modified lipase of the present invention.

As the lipase, there may be employed those existing in pancreatic juice or gastric juice of animals and those produced by fungi, yeasts and bacteria. Also, esterases which generally catalyze decomposition and synthesis of esters are included.

The modified lipase of the present invention, which is modified with a straight chain comprising a substituted polyalkylene glycol having both properties of hydrophobicity and hydrophilicity, is soluble in both water and organic solvents, and the higher structure specific in lipase is also protected by these straight chains, whereby deactivation through contact with organic solvents is prevented.

The polyalkylene glycol may include polyethylene glycols and polypropylene glycols, preferably polyethylene glycols having molecular weights of 5000 or higher. As the hydrophobic groups, there may be employed alkyl groups such as methyl, ethyl, hexyl, octyl, nonyl and the like and phenyl groups such as phenyl, alkyl-substituted phenyl, phenyl-substituted phenyl, styryl-substituted phenyl, and the like, preferably methyl. These hydrophobic groups are ether bonded to one of the terminal hydroxyl groups of the polyalkylene glycol.

For having the other terminal end of the polyalkylene glycol bonded to the lipase molecule, the polyalkylene glycol may be led to an active derivative according to the known methods for immobilization of enzymes on carriers, such as the alkylation method, the acid azide method, the diazo method, the condensation method, etc., which is then allowed to react with the free amino groups or carboxyl groups in lipase to effect bonding.

As the alkylation method, there may be mentioned the method in which the polyalkylene glycol is activated by being led to a triazine derivative or an acetyl derivative. In the following description, P-OH shows the polyalkylene glycol having a hydrophobic group at the terminal end, E shows a lipase molecule, and the amino group or carboxyl group bonded to E shows a free group in the lipase molecule.

(1) P-OH is allowed to react with cyanuric chloride in the presence of a base in an inert solvent to obtain an active derivative in which one or two P-OH straight chain is bonded. The active derivative is allowed to react with lipase in a buffer to be bonded to the free amino group in lipase.

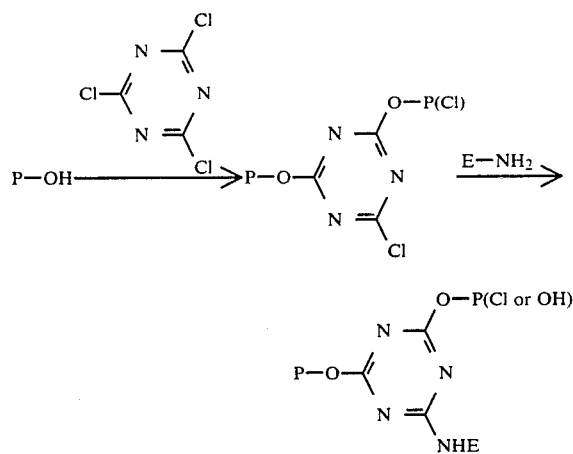

(2) The reaction between P-OH and bromoacetyl bromide is carried out in dibromoacetic acid-dioxane to obtain P-bromoacetate. The acetyl derivative is allowed to react with lipase. P-dibromosuccinate prepared by use of dibromosuccinic anhydride can also be reacted with lipase.

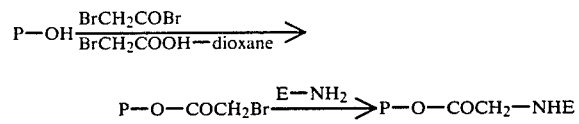

According to the acid azide method, P-OH is allowed to react with chloroacetic anhydride, then with diazomethane to obtain P-acetic acid methyl ether, which is treated with hydrazine to obtain a corresponding hydrazide followed by treatment with sodium nitrite to obtain an acid azide derivative. The active derivaive is reacted with lipase to be bonded to free amino groups in lipase.

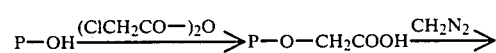

-continued

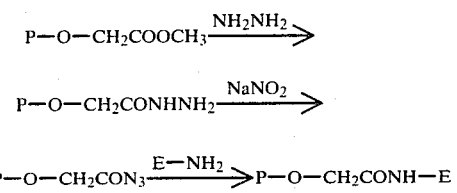

According to the diazo method, for example, P-OH is allowed to react with isatoic acid anhydride to obtain an anthranilic acid ester, which is then treated with sodium nitride to be converted to a diazonium derivative, followed by diazo-coupling with lipase.

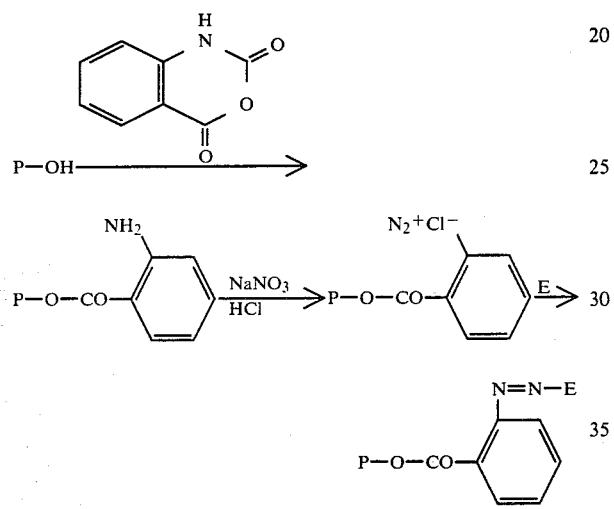

The terminal hydroxyl group of P-OH can be converted to amino group. According to this method, for example, P-OH is allowed to react with tosyl chloride to form P-OH-tosylate, which is then reacted with a phthalimide salt to obtain a N-P-substituted phthalimide, followed by treatment with hydrazine to obtain ω-amino-P-OH. The amino derivative can be directly bonded to carboxyl group in lipase with a carbodiimide reagent or Woodward reagent K. Alternatively, P-OH-tosylate or P-OHω-bromide obtained by the reaction with a halogenating agent may be converted to P-OHω-azide with sodium azide, followed by hydrogen reduction to obtain ω-amino P-OH.

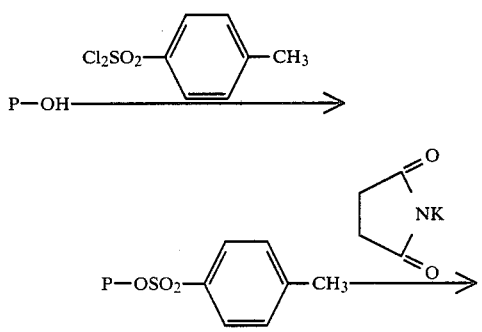

-continued

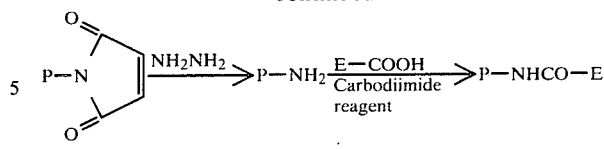

Other than the methods as described above, the carboxylic acid derivative of P-OH can be allowed to react with a bromacetic acid ester in the presence of potassium t-butoxide, followed by hydrolysis, to obtain P-carboxymethyl ether. The carboxylic acid derivative is reacted with N-hydroxysuccinic acid by utilizing a carbodiimide reagent to obtain the corresponding succinimide ester, which is then reacted with amino groups in lipase.

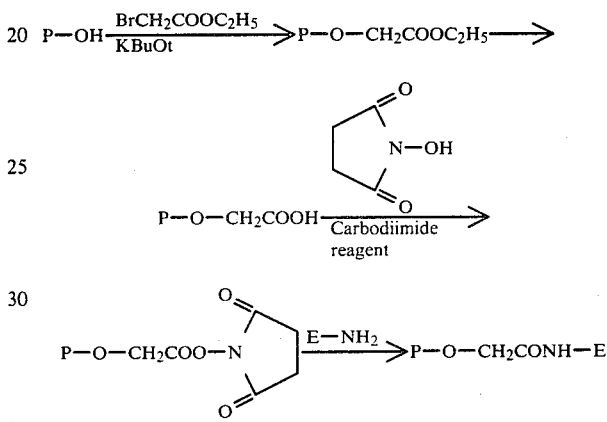

Of the above modified lipases, the modified lipases in which the amino groups of lipase are partially substituted with the groups of the formula:

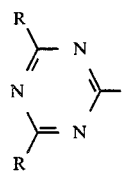

wherein R represents a polyalkylene glycol group having a hydrophobic group at the terminal end, are particularly preferred for the object of the present invention. More preferable lipases are modified lipases as mentioned above, in which there is substituted 2,4-bis(methoxypolyoxyethylene)-6-triazine of which polyoxyethylene moiety has a molecular weight of 5000 or more.

The modified lipase prepared as described above can be purified according to conventional procedures, lyophilized and stored. The percentage of the polyalkylene glycol added in the modified lipase can be measured by determining the unaltered amino groups with trinitrobenzenesulfonic acid, and those containing polyalkylene glycol added to about 50 to 70% of amino groups in lipase molecules are most preferred.

The modified lipase of the present invention can effect various reactions such as decomposition and synthesis of esters, interesterification and aminolysis in organic solvents.

Reactions such as decomposition or synthesis of esters with the modified lipase may be conducted in organic solvents capable of dissolving the modified lipase, the substrate and the product. Such solvents may preferably be, for example, aromatic hydrocarbons such as benzene, toluene or xylene and chlorinated hydrocarbons such as chloroform, 1,1,1-trichloroethane, trichloroethylene, tetrachloroethylene and the like. These solvents should preferably contain a small amount of water also in ester synthesis.

During synthesis of an ester, the substrate carboxylic acid may include various kinds of carboxylic acids, for example, $C_2$ to $C_{24}$ saturated or unsaturated fatty acids such as butyric acid, lauric acid, palmitic acid, stearic acid, oleic acid, linoleic acid, arachidonic acid, prostaglandins. Alcohols may include $C_{1-24}$ primary or secondary fatty alcohols, such as methyl alcohol, ethyl alcohol, octyl alcohol, lauryl alcohol, stearyl alcohol, ethylene glycol, glycerine; $C_7$-$C_9$ aromatic fatty alcohols such as benzyl alcohol; sterols such as sitosterol, cholesterol and ergosterol. In general, among fatty alcohols, more hydrophobic alcohols with larger number of carbon atoms are more preferable. When ethyl alcohol is used, the highest activity can be obtained by making the final concentration of ethyl alcohol in an organic solvent 5%. On the other hand, as the starting material ester, it is preferred to employ an ester of the above fatty acid with an alcohol or a triglyceride. In particular, modification of a fat can be effected by carrying out acidolysis which interchanges a part of the fatty acids in a triglyceride with fatty acid groups. It is also possible to effect alcoholysis in which the alcohol moiety of an ester is interchanged with other alcohols.

In the ester synthesis reaction, water is formed with increase of the product and stopped when the reaction reaches equilibrium, and therefore it is preferred to complete the reaction while removing water from the reaction system in a conventional manner.

The present invention is illustrated by referring to the following Examples.

EXAMPLE 1

(1) Synthesis of 2,4-bis(methoxypolyoxyethylene)-6-chloro-s-triazine:

In 100 ml of anhydrous benzene containing 10 g of anhydrous sodium carbonate was dissolved 20 g of monomethoxy polyethylene glycol (molecular weight of PEG moiety: 5000), and the reaction was carried out under reflux at 80° C. for 30 minutes. Then, with addition of 65 mg of 2,4,6-trichloro-s-triazine, the reaction was carried out under reflux at 80° C. for 24 hours. The reaction residue was filtered off and 300 ml of petroleum ether was added to form precipitates, and the precipitates were washed several times with petroleum ether to prepare 2,4-bis(methoxypolyoxyethylene)-6-chloro-s-triazine.

(2) Preparation of lipase modified with 2,4-bis(methoxypolyoxyethylene)-6-triazine:

To 2 ml of 0.4 M borate buffer (pH 10.0) containing 10 mg of lipoprotein lipase obtained from *Pseudomonas fluorescence*, 400 mg of 2,4-bis(methoxypolyoxyethylene)-6-chloro-s-triazine was added and the reaction was carried out at 37° C. for one hour, followed by purification in a conventional manner to obtain a modified lipase in which 52% of the amino groups in lipase molecules were modified with the above triazine derivative. This was dialyzed sufficiently against water and lyophilized.

(3) Synthesis of lauryl stearate:

In 400 μl of benzene saturated with water (containing about 30 mM water), stearic acid and lauryl alcohol at various concentrations as shown in the Figure were dissolved, and to each of these solutions was added 100 μl of the solution of the modified lipase (1.5 mg/ml) obtained in the above (2) in benzene saturated with water. Then, the reaction was carried out by incubation at 37° C. for 20 minutes. After the reaction, 100 μl of 0.2N sulfuric acid solution in benzene was added to stop the reaction, and thereafter 1 ml of 0.25N aqueous sodium hydroxide solution, 2 ml of petroleum ether and 600 μl of methyl alcohol were added. After separation of the desired ester produced, the amount of the ester formed was determined colorimetrically in a conventional manner.

Figure 2:
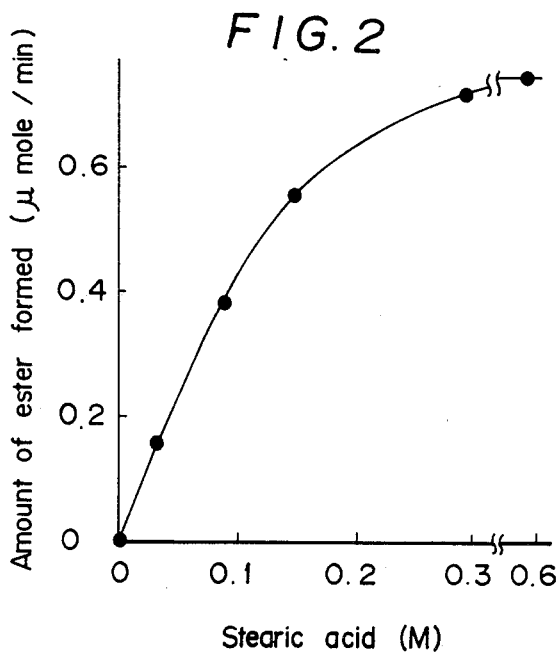

FIG. 1 shows the amount of the ester formed when the concentration of stearic acid was made constantly 0.3 M and the concentration of lauryl alcohol was varied, and FIG. 2 the amount of the ester formed when the concentration of lauryl alcohol was made constantly 0.45 M and the concentration of stearic acid was varied. From these Figures, the modified lipase exhibited the maximum ester synthesis activity of 4.5 μmole/min./mg-protein.

(4) Solubility and enzymic activity of the modified lipase in various organic solvents:

Solubility was determined by adding 1 mg of the lyophilized modified lipase (modification percentage: 55 obtained in the above (2) in 1 ml of an organic solvent saturated with water and, after stirring, subjecting the mixture to centrifugation to remove insolubles and measuring the dissolved protein content. On the other hand, enzymic activity was determined by adding 1 mg/ml of the modified lipase obtained in the above (2) into a solution of lauric acid and lauryl alcohol dissolved in 50 μl of each solvent, maintaining the mixture at 25° C. for 20 minutes and quantifying the lauryl laurate synthesized. The results are shown in Table 1. Here, the enzymic activity in benzene is 7.1 μmole/min./mg-protein.

TABLE 1

| Solvent | Solubility (mg/ml) | Relative enzymic activity in ester synthesis |
|---|---|---|
| Benzene | 0.95 | 100 |
| Toluene | 1.0 | 87 |
| Chloroform | 1.0 | 67 |
| 1,1,1-Trichloroetane | 0.75 | 380 |
| Trichloroethylene | 1.0 | 48 |
| Tetrachloroethylene | 0.23 | 48 |

While unmodified lipase cannot be dissolved in the above solvents at all, the modified lipase becomes soluble in the above solvents, as apparently seen from the above Table. It can be seen that the modified lipase can exhibit high activity in organic solvents, particularly trichloroethane and benzene. The modified lipase was also found to be stable in benzene and retained 40% of the ester synthesis enzymic activity after 150 days. Further, by addition of n-hexane or petroleum ether to the modified lipase solution, it can be recovered in 100% recovery as the precipitate from the organic solvent without deactivation of the enzymic activity.

(5) Synthesis of sitosterol ester of lauric acid:

To 1 ml of a 0.25 M sitosterol solution in benzene saturated with water, 400 μl of 1.8 M lauric acid solution in benzene saturated with water was added, followed by further addition of a solution of the modified lipase obtained in the above (2) (0.74 mg/ml) in benzene, saturaed with water, and the reaction was carried out at 37° C. for 50 hours. After completion of the reaction, the title ester formed was separated by silica gel chromatography and recrystallized to give 3 mg of the purified product of the title ester.

(6) Alcoholysis of trilaurin with ethyl alcohol:

To 200 μl of a 0.2 M trilaurin solution in benzene saturated with water, 100 μl at varied concentration of ethyl alcohol solution in benzene saturated with water was added, followed by further addition of 100 μl of a solution of the modified lipase obtained in the above (2) (0.27 mg/ml) in benzene saturated with water, and the reaction was carried out at 37° C. for one hour. After completion of the reaction, the product was separated by thin layer chromatography, and the ethyl laurate formed was quantified colorimetrically. As the result, the alcoholysis activity exhibited the maximum value of about 0.7 μmole/min./mg-protein in about 1% ethyl alcohol.

(7) Acidolysis of methyl butyrate with lauric acid:

To 50 μl of 1.2 M lauric acid solution in benzene saturated with water was added 50 μl of methyl butyrate, followed by further addition of 100 μl of a solution of the modified lipase obtained in the above (2) (0.5 mg/ml) in benzene saturated with water, and the reaction was carried out by incubation at 37° C. for 20 minutes. After completion of the reaction, methyl laurate formed was separated by thin layer chromatography, extracted with petroleum ether and subjected to colorimetric quantitative determination of methyl laurate according to the conventional method. As the result, the acidolysis activity of the modified lipase exhibited about 1 μmole/min./mg-protein.

(8) Decomposition of trilaurin:

To a solution of 100 mM trilaurin dissolved in 200 μl of benzene saturated with water, 1 mg/ml of the modified lipase obtained in the above (2) was added, and the mixture was maintained at 37° C. for 20 minutes. Then, the amount of the lauric acid liberated was determined to find that the modified lipase exhibited an enzymic activity of 1.6 μmole/min./mg-protein.

EXAMPLE 2

(1) Methoxypolyoxyethylene-acetic acid azide ether:

A methoxypolyoxyethylene-acetic acid ether was obtained from the reaction of 2.0 g of a monomethoxypolyethylene glycol (molecular weight of PEG moiety: 5000) with 5 ml of chloroacetic anhydride at room temperature, and 5 ml of 0.2 M diazomethane solution in ether was added thereto followed by the reaction at a temperature of 0° C. or lower to obtain the corresponding methyl ester. To 2.0 g of the methyl ester, 15 ml of hydrazine hydrate and 300 ml of methanol were added and the reaction was carried out under reflux to give the corresponding hydrazide.

The hydrazide (1.0 g) was dissolved in dil. hydrochloric acid and cooled. Under stirring, 9 ml of 0.5 M sodium nitrite was added dropwise and the mixture was left to stand at room temperature for about 15 minutes to obtain an ether of methoxypolyoxyethylene-acetic acid azide.

(2) Preparation of lipase modified with methoxypolyoxyethylene methoxycarbonyl:

A solution of 5 mg of a lipase obtained from *Pseudomonas fluorescence* dissolved in 2 ml of a sodium phosphate buffer (pH 10) was mixed with 1.0 g of the acid azide derivative obtained in the above 1), followed by the reaction under stirring at room temperature for 2 hours. Then, 100 ml of a 0.1 M borate buffer (pH 8.5) was added to the reaction mixture and the mixture was subjected to ultrafiltration with Amicon PM-30 membrane filter. After thorough washing with phosphote buffer, the product was dialyzed sufficiently against water and lyophilized.

(3) Activity of the modified lipase:

The activity of the modified lipase obtained in the above (2) was measured according to the method of Example 1 (3) to exhibit 1 μmole/min./mg-protein.

EXAMPLE 3

(1) Synthesis of methoxypolyoxyethylene-dibromosuccinate:

A solution of 1.0 g of methoxypolyethylene glycol in 10 ml of anhydrous benzene was mixed with 0.5 g of dibromosuccinic anhydride, followed by the reaction under stirring overnight. Then, the reaction mixture was filtered and the filtrate concentrated under reduced pressure to give methoxypolyoxyethylene-dibromosuccinate. This was then purified repeatedly with benzene-petroleum ether.

(2) Preparation of the modified lipase in which a methoxypolyoxyethylene is bonded through acetyl group:

To a solution of 5 mg of a lipase obtained from *Pseudomonas fluorescence* dissolved in 2 ml of a phosphate buffer (pH 7.0), 500 mg of the methoxypolyethylenedibromosuccinate obtained in the above (1) was added, while setting the starting pH and maintaining it at pH 7.0, following subsequently the same procedure as in Example 2 - (2), to obtain a modified lipase.

(3) Activity of the modified lipase:

The modified lipase obtained in the above (2) was confirmed to synthesize the corresponding ester from stearic acid and lauryl alcohol in benzene solution saturated with water.

EXAMPLE 4

(1) Synthesis of diazonium salt of anthranilic acid ester of methoxypolyoxyethylene:

To a solution of 1.0 g of methoxypolyethylene glycol dissolved in 10 ml of anhydrous benzene containing 1.0 g of sodium carbonate, 0.25 g of isatoic anhydride was added and the mixture was left to stand overnight, followed by filtration of the solution to obtain the corresponding isatoate. Hydrochloric acid was added to the aqueous solution of this ester and the mixture was cooled to 4° C. and 0.5 M sodium nitrite was added dropwise under stirring until $NO_2^-$ was confirmed to remain. The diazotized product was filtered, washed with cold 0.01N hydrochloric acid and further with water.

(2) Modified lipase in which methoxypolyoxyethylene is bonded through diazobenzoyl group:

A solution of 25 mg of a lipase obtained from *Pseudomonas fluorescence* dissolved in 5 ml of a phosphate buffer (pH 7 to 7.5) was cooled to 0° to 2° C., and the above diazotized solution obtained in the above (1) was added dropwise. The reaction was carried out, while maintaining pH start at 7, for 2 hours. Following subsequently the procedure of Example 2 - (2), a modified lipase was obtained.

(3) Activity of the modified lipase:

The modified lipase obtained in the above (2) was confirmed to synthesize the corresponding ester from stearic acid asnd lauryl alcohol in the benzene solution saturated with water.

EXAMPLE 5

(1) Synthesis of ω-amino-methoxypolyethylene glycol:

To a solution of 3 g of methoxypolyethylene glycol dissolved in 50 ml of chloroform, 2 ml of pyridine and 3.8 g of tosyl chloride were added, and the reaction was carried out under reflux for 22 hours, followed by distillation under reduced pressure. The reaction residue was dissolved in water, filtered and extracted with chloroform. The extract was dried over anhydrous sodium sulfate, followed by evaporation of the solvent, and the residue was dissolved in chloroform and subjected to precipitation with ether for purification.

The tosylated product (3 g) was dissolved in dimethylformamide, admixed with 1 g of potassium phthalimide and the reaction mixture was allowed to react under a nitrogen stream under reflux at 120° C. for 3 days. The corresponding phthalimide derivative obained was dissolved in 10 ml of chloroform and, with addition of 50 ml of hydrazine hydrate, subjected to the reaction at 70° C. for 3 days, followed by purification in a conventional manner of the resultant condensate. Further, the product was applied to a Sephadex C-25 (H+ form) column of 4×60 cm, and subjected to gradient elution with sodium chloride of 0 to 30 mM to fractionate ω-amino product. The fractions were extracted with chloroform and dried over anhydrous sodium sulfate to obtain the title product.

(2) Modified lipase in which methoxypolyoxyethylene is bonded through amide bonding:

To a solution of 500 mg of the ω-amino-methoxypolyethylene glycol obtained in the above (1) dissolved in 3 ml of a phosphate buffer (pH 6.0), 10 mg of a lipase obtained from Pseudomonas fluorescence was added, followed by addition of 60 mg of ethyldimethylaminopropyl carbodiimide. While maintaining the pH start at 6.0, the reaction was carried out for one hour and then stopped with addition of an excessive amount of acetic acid salt, and the modified lipase obtained was purified according to the conventional method.

(3) Activity of the modified lipase:

The modified lipase obtained in the above (2) was confirmed to synthesize the corresponding ester from stearic acid and lauryl alcohol in the benzene solution saturated with water.

EXAMPLE 6

(1) Ether of methoxypolyoxyethylene-acetic acid succinimide ester:

A methoxypolyethylene glycol (14 g) and potassium t-butoxide (10 g) were added to 150 ml of t-butyl alcohol and dissolved by heating to 40° C. To the resultant solution was added 5 ml of ethyl bromoacetate over 10 minutes, followed by further stirring for 2 hours. The mixture was distilled under reduced pressure, and the product dissolved in 100 ml of 1N sodium hydroxide, adjusted to pH 2 with hydrochloric acid after 2 hours, followed by extraction with chloroform to obtain the corresponding acetic acid ether. The acetic acid ether (15 g) was dissolved in 130 ml of anhydrous dioxane and 3.5 g of N-hydroxysuccinimide was added thereto, followed by further addition of 6 g of dicyclohexyl carbodiimide to carry out the reaction at room temperature overnight. The precipitate obtained was filtered off and addition of 500 ml of hexane to the filtrate gave the product. The product was dissolved in 100 ml of benzene, and the purification procedure to precipitate with hexane was repeated to obtain the title acetic acid succinimide ester ether.

(2) Preparation of lipase modified with methoxypolyoxyethylene methoxycarbonyl:

To a solution of 10 mg of a lipase obtained from Pseudomonas fluorescence dissolved in 2 ml of a borate buffer (pH 9.0) was added 500 mg of the acide imide ester ether derivative obtained in (1), and the reaction was carried out at 37° C. for 12 hours. After completion of the reaction, the product was purified by ultrafiltration by use of Amicon PM-30 to prepare the title modified lipase.

(3) Activity of the modified lipase:

The modified lipase obtained in the above (2) was confirmed to synthesize the corresponding ester from stearic acid asnd lauryl alcohol in the benzene solution saturated with water.

I claim:

1. A modified lipase, comprising lipase molecules which are partially substituted with an active derivative of a polyalkylene glycol having a hydrophobic group at the terminal end.

2. The modified lipase according to claim 1, wherein the polyalkylene glycol is a polyethylene glycol having a molecular weight of 5,000 or more.

3. The modified lipase according to claim 1, wherein the hydrophobic group at the terminal end is an alkyl group or an aryl group.

4. The modified lipase according to claim 1, wherein the active derivative is a triazine derivative, an acetyl derivative, a diazonium derivative, an amino derivative or a carboxylic acid derivative.

5. The modified lipase according to claim 1, wherein the amino groups in the lipase molecules are partially substituted with a group of the formula:

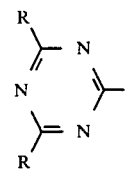

wherein R represents a polyalkylene glycol group having a hydrophobic group at the terminal end.

6. The modified lipase according to claim 5, which is substituted with a 2,4-bis(methoxypolyoxyethylene)-6-triazine of which the polyoxyethylene moiety has a molecular weight of 5,000 or more.

7. A process for producing an ester, which comprises effecting in an organic solvent (i) esterification by allowing a carboxylic acid to react with an alcohol or (ii) interesterification by allowing an ester of carboxylic acid to react with other carboxylic acid or an alcohol, in the presence of a modified lipase obtained by allowing an active derivative of a polyalkylene glycol having a hydrophobic group at the terminal end to react with a lipase.

8. The process of claim 1, wherein the polyalkylene glycol is a polyethylene glycol having a molecular weight of 5,000 or more.

9. The process of claim 1, wherein the hydrophobic group at the terminal end is an alkyl group or an aryl group.

10. The process of claim 1, wherein the active derivative is a triazine derivative, an acetyl derivative, a diazonium derivative, an amino derivative or a carboxylic acid derivative.

11. The process of claim 1 wherein lipase molecules contain amino groups which are partially substituted with a group of the formula:

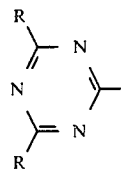

wherein R represents a polyalkylene glycol group having a hydrophobic group at the terminal end.

12. The process of claim 11, wherein said modified lipase is substituted with a 2,4-bis(methoxyoxyethylene)-6-triazine of which the polyoxyethylene moiety has a molecular weight of 5,000 or more.

13. A modified lipase, comprising lipase molecules which are partially substituted with an active derivative of a polyalkylene glycol having a hydrophobic group at the terminal end which promotes (i) esterification by allowing a carboxylic acid to react with an alcohol or (ii) interesterification by allowing an ester of a carboxylic acid to react with other carboxylic acid or an alcohol, in an organic solvent.

* * * * *